United States Patent [19]
Brown

[11] Patent Number: 5,817,474
[45] Date of Patent: *Oct. 6, 1998

[54] COMPOSITIONS AND METHODS FOR PROTEIN STRUCTURAL DETERMINATIONS

[75] Inventor: Jonathan Miles Brown, Baltimore, Md.

[73] Assignee: Martek Biosciences Corporation, Columbia, Md.

[ * ] Notice: The term of this patent shall not extend beyond the expiration date of Pat. No. 5,627,044.

[21] Appl. No.: 680,637

[22] Filed: Jul. 16, 1996

Related U.S. Application Data

[60] Division of Ser. No. 307,768, Sep. 27, 1994, Pat. No. 5,627,044, which is a continuation-in-part of Ser. No. 14,243, Feb. 5, 1993, Pat. No. 5,393,669.

[51] Int. Cl.$^6$ .............................. C12Q 1/02; C12P 13/14; C12P 13/12; C12P 13/10
[52] U.S. Cl. ................................ 435/29; 435/4; 435/110; 435/113; 435/114; 435/253.6; 436/86; 436/15
[58] Field of Search ................................ 435/29, 4, 110, 435/113, 114, 253.6; 436/86, 15

[56] References Cited

U.S. PATENT DOCUMENTS

| | | | |
|---|---|---|---|
| 4,182,656 | 1/1980 | Ahnell et al. | 435/29 |
| 4,281,061 | 7/1981 | Zuk et al. | 435/4 |
| 4,478,934 | 10/1984 | Sato et al. | 435/4 |
| 5,168,225 | 12/1992 | Yamazaki et al. | 435/29 |
| 5,393,669 | 2/1995 | Brown | 435/29 |
| 5,478,729 | 12/1995 | Van Atta et al. | 435/4 |

OTHER PUBLICATIONS

Refsum et al., "Radioenzymic Determination of Homocysteine in Plasma and Urine", Clin. Chem. 31(4), pp. 624–628 (1985).
Hemmila, "Fluoroimmunoassays and Immunofluorometric Assays", Clin Chem. 31/3, pp. 359–370 (1985).
Harlow et al., "Antibodies a Laboratory Manual", Chapter 14, Cold Spring Harbor Laboratory, 1988.
Ueland et al., "Total Homocysteine in Plasma or Serum: Methods and Clinical Applications", Clin. Chem. 39/9, pp. 1764–1779, (1993).
Andersson et al., "Homocysteine and Other Thiols Determined in Plasma by HPLC and Thiol–Specific Postcolumn Derivatization", Clin. Chem. 39/8, pp. 1590–1597 (1993).
G.J. Cox, J. Biol. Chem., 78 (1928), pp. 475–479.
J.D. Watson and F.H.C. Crick, Nature, 171 (1953), pp. 737–738.
M.F. Perutz et al., Nature, 185 (1960), pp. 416–422.
D.M. LeMaster and F.M. Richards, Analytical Biochemistry, 122 (1982), pp. 238–247.
L.E. Kay et al., Science, 249 (1990), pp. 411–414.
P.C. Driscoll et al., Nature, 353 (1991), pp. 762–765.
K. Appelt et al., Journ. of Med. Chem., 34 (1991), pp. 1925–1934.
V.L. Hsu and I.M. Armitage, Biochemistry, 31 (1992), pp. 12778–12784.
A.P. Hansen et al., Biochemistry, 31 (1992), pp. 12713–12718.
S.J. Archer et al., Biochemistry, 32 (1993), pp. 1152–1163.
S.J. Archer et al., Biochemistry, 32 (1993), pp. 1164–1171.
Patents Abstracts of Japan, vol. 14, No. 503, issued Nov. 02, 1990, Nakamura et al., "Method of Analyzing Protein Structure", 20 Aug. 1990, Abs. grp. No. P1126, ABS Abs of JP 01–29261, see entire abstract.
Derwent Abstract of Japanese Patent JP04046143, issued Feb. 17, 1992, Hitachi KK, "Synthesis of isotape multi–labelled aminoacid in improved yield–by reacting aldehyde(s) ammonium . . . hydrolyzing", see entire abstract.

Primary Examiner—Louise N. Leary
Attorney, Agent, or Firm—Rothwell, Figg, Ernst & Kurz

[57] ABSTRACT

A method for determining three-dimensional structural information of a protein which involves producing the protein in a form substantially labeled with $^{13}$C of $^{15}$N or both substantially labeled with $^{15}$N and $^{13}$C and partially labeled with $^2$H and subjecting the protein to nuclear magnetic resonance spectroscopic analysis. The isotopically labeled protein is produced by a method which involves producing a substantially labeled microbial protein hydrolysate, subjecting the protein hydrolysate to cation exchange chromatography to produce a partially purified labeled amino acid mixture, subjecting the partially purified labeled amino acid mixture to anion exchange chromatography to produce a purified labeled amino mixture and supplementing the purified labeled amino acid mixture with isotopically labeled cysteine and optionally with isotopically labeled glutamine and asparagine.

28 Claims, No Drawings

COMPOSITIONS AND METHODS FOR PROTEIN STRUCTURAL DETERMINATIONS

This is a divisional of application Ser. No. 08/307,768, filed Sep. 27, 1994, now U.S. Pat. No. 5,321,549, which is a Continuation-in-Part of application Ser. No. 08/014,243, filed Feb. 5, 1993, now U.S. Pat. No. 5,393,669.

FIELD OF THE INVENTION

This invention is concerned with the determination of the three-dimensional structure of biological macromolecules, especially proteins. In particular, it is concerned with novel compositions and methods for the determination, by NMR spectroscopy, of the three-dimensional structure of proteins expressed in cultures of mammalian or insect cells.

BACKGROUND OF THE INVENTION

For many years, there has been intense interest in the determination of the three-dimensional structure of biological macromolecules, particularly proteins. So-called "structure-function" studies have been carried out with a view to determining which structural features of a molecule, or class of molecules, are important for biological activity. Since the pioneering work of Nobel laureates, Perutz and coworkers on the structure of hemoglobin (Perutz, M. F. et al., *Nature*, 185, 416 –422 (1960)) and Watson and Crick on the structure of DNA (Watson, J. D. and Crick, F. H. C., *Nature*, 171, 737 (1953)), this field has been of major importance in the biological sciences.

More recently, there has evolved the concept of "rational drug design." This strategy for the design of drugs involves the determination of the three-dimensional structure of an "active part" of a particular biological molecule, such as a protein. The biological molecule may, for example, be a receptor, an enzyme, a hormone, or other biologically active molecule. Knowing the three-dimensional structure of the active site can enable scientists to design molecules that will block, mimic or enhance the natural biological activity of the molecule. (Appelt, K., et al., *J. Med. Chem.*, 34, 1925 (1991)). The determination of the three-dimensional structure of biological molecules is therefore also of great practical and commercial significance.

The first technique developed to determine three-dimensional structures was X-ray crystallography. The structures of hemoglobin and DNA were both determined using this technique. X-ray crystallography involves bombarding a crystal of the material to be examined with a beam of X-rays which are refracted by the atoms of the ordered molecules in the crystal. The scattered X-rays are captured on a photographic plate, which is then developed using standard techniques. The diffracted X-rays are thus visualized as a series of spots on the plate, and from this pattern, the structure of the molecules in the crystal can be determined. For larger molecules, it is also necessary to crystallize the material with a heavy ion, such as ruthenium, in order to remove ambiguity due to phase differences.

More recently, another technique, nuclear magnetic resonance ("NMR") spectroscopy, has been developed to determine the three-dimensional structures of biological molecules, and particularly proteins. NMR spectroscopy was originally developed in the 1950's and has evolved into a powerful procedure for analyzing the structure of small compounds, such as those with a molecular weight of ≦1000 daltons. Briefly, the technique involves placing the material (usually in a suitable solvent) in a powerful magnetic field and irradiating it with a strong radio signal. The nuclei of the various atoms will align themselves with the magnetic field until energized by the radio signal. They then absorb this energy and re-radiate (resonate) it at a frequency dependent on i) the type of nucleus and ii) the chemical environment (determined largely by bonding) of the nucleus. Moreover, resonances can be transmitted from one nucleus to another, either through bonds or through three dimensional space, thus giving information about the environment of a particular nucleus and nuclei in the vicinity of it.

However, it is important to recognize that not all nuclei are NMR active. Indeed, not all isotopes of the same element are active. For example, whereas "ordinary" hydrogen, $^1H$, is NMR active, heavy hydrogen (deuterium), $^2H$, is not. Thus, any material that normally contains $^1H$ hydrogen can be rendered "invisible" in the hydrogen NMR spectrum by replacing all the $^1H$ hydrogens with $^2H$. It is for this reason that NMR spectra of water-soluble materials are determined in solution in $^2H_2O$, so as to avoid the water signal.

Conversely, "ordinary" carbon, $^{12}C$ is NMR inactive whereas the stable isotope $^{13}C$, present to about 1% of total carbon in nature, is active. Similarly, "ordinary" nitrogen, $^{14}N$, is NMR inactive whereas the stable isotope $^{15}N$, again present to about 1% of total nitrogen in nature, is active. For small molecules, it was found that these low level natural abundancies were sufficient to generate the required experimental information, provided that the experiment was conducted with sufficient quantities of materials and for sufficient time.

As advances in hardware and software were made, the size of molecules that could be analyzed by these techniques increased to about 10,000 daltons, the size of a small protein. The application of NMR spectroscopy to protein structural determinations therefore began only a few years ago. It was quickly realized that this size limit could be raised by substituting the NMR active stable isotopes $^{15}N$ and $^{13}C$ into the proteins in place of the NMR inactive isotopes $^{14}N$ and $^{12}C$. A method of achieving this substitution was to grow microorganisms capable of producing the proteins in growth media labeled with these isotopes.

Over the past two or three years, $^{15}N$-labeling and $^{13}C$-labeling of proteins, have raised the analytical size limit to approximately 15 kd and 25 kd respectively. This isotopic substitution has been accomplished by growing a bacterium or yeast, transformed by genetic engineering to produce the protein of choice, in a growth medium containing $^{13}C$ and/or $^{15}N$ labeled substrates. In practice, these media usually consist of $^{13}C$ labeled glucose and/or $^{15}N$ labeled ammonium salts. (Kay, L. et al., *Science*, 249, 411 (1990) and references therein.) Recently, bacterial and yeast nutrient media containing labeled protein hydrolyzates have been described. See International Patent Application, publication no. WO 90/15525, published Dec. 27, 1990.

While $^{13}C$ and $^{15}N$ labeling has enabled NMR structural determinations for proteins substantially larger than those previously amenable to such techniques, proteins larger than about 25 kd present ambiguous results. At this size, many of the resonances from the individual atoms become too broad to resolve. In a recent publication, it has been reported that triple-labeling, i.e., the partial incorporation of deuterium, $^2H$, as well as $^{13}C$ and $^{15}N$ isotopes, narrowed significantly the otherwise broadened lines in a larger molecule. Bax, *J. Am. Chem. Soc.*, 115:4369 (1993). Triple-labeled media are therefore preferred for the preparation of labeled forms of proteins large than about 25 kd for NMR structural determinations. For bacterial proteins, partial $^2H$-labeling can be achieved by culturing the bacteria in the presence of a mixture of $H_2O$ and $^2H_2O$. This approach is unsatisfactory, however, for the production of suitably labeled mammalian proteins.

Heretofore, compositions and methods for NMR structural determinations have suffered from a significant limitation. Most proteins of interest in structure-function studies are mammalian in origin. Moreover, virtually all proteins of interest in rational human drug design are mammalian, i.e., human, in origin. Yet neither X-ray crystallography nor NMR spectroscopy have had widespread use in examining proteins produced from mammalian cells. X-ray crystallography, by definition, requires crystalline material, yet mammalian cell proteins are notoriously difficult to crystallize. To date, only a few antibodies and mammalian cell-derived receptors have been crystallized in a form suitable for crystallography. Those that have been crystallized have usually been selected fragments of a molecule. Information derived from molecular fragments is viewed with caution, as it is never known whether the structure of the part of the main molecule on its own is the same as that of that part of the molecule in the whole molecule. Moreover, X-ray crystallography is inapplicable in those frequent instances in which crystalline material cannot be obtained.

NMR structural studies have hitherto been limited by the necessity of expressing the labeled proteins in bacteria or yeast. However, most mammalian proteins contain significant post-translational modifications that cannot be effected in bacterial and yeast systems. That is to say, they are appropriately folded and cross-linked with disulfide bridges, may have attached side chains of oligosaccharides and may be proteolytically cleaved to active forms. Bacterial or yeast-produced proteins frequently do not possess the biological activity of mammalian cell-produced proteins. Indeed, in some cases, mammalian proteins cannot be produced in bacteria at all. For these reasons, the biotechnology industry moved from bacterial expression systems to mammalian ones in the mid 1980's to produce recombinant therapeutic proteins, such as tissue plasminogen activator, Factor VIII:C, erythropoietin and the like. Parts of some mammalian cell proteins have been studied by NMR by cloning the gene for a fragment of the molecule of interest into a bacterium, and expressing the fragment in isotopically labeled form by growth of the bacterium in an isotopically labeled medium. Again, only those parts of a molecule of choice that can be expressed in bacteria have been susceptible to study in these systems (e.g. see Driscoll, P. C., et al., *Nature*, 353, Oct. 24, 1991). Because of the lack of post-translational modifications inherent in bacterial expression, the molecular parts examined have been produced in the absence of such post-translational modifications such as glycosylation etc., again leading to doubt as to the value of the structures obtained. As with X-ray crystallography, there have also been subsequent doubts as to the value of structural information obtained from protein fragments.

Host-vector systems utilizing both mammalian cells and insect cells have been developed. Mammalian cell lines, such as Chinese hamster ovary (CHO) cells, COS cells and insect-cell lines, such as the *Spodoptera frugiperda* cell lines SF9 and SF21 (Luckow, V. A. and Summers, M. D., *Biotechnology*, 6 47–55 (1988)), have been found to produce recombinant mammalian proteins with post-translational modifications similar to those of the natural protein.

NMR studies on mammalian and insect cell-produced proteins have been of limited value, as no means of universally incorporating stable isotopes such as $^{13}C$ or both $^{13}C$ and $^{15}N$ in an analogous manner to that for bacteria have been available. Whereas bacteria can grow on a simple mixture of glucose and salts, mammalian and insect cells require, in addition to glucose, all of the amino acids essential for growth. For instance, for the successful production of a universally $^{13}C$ and/or $^{15}N$ labeled protein from mammalian cells all of these amino acids would have to be present and all would have to be universally labeled with $^{13}C$ and/or $^{15}N$.

One theoretical way of producing an isotopically labeled medium would be to use a simple hydrolysate of an isotopically labeled protein. Unfortunately, hydrolysis of proteins to the constituent amino acids also leads to the concomitant formation of side products that are toxic to mammalian cells. Use of unpurified hydrolysates has been found to lead to rapid death of the cells. Moreover, conventional hydrolysis procedures destroy certain essential amino acids, and available means for preventing such destruction often result in toxic effects. On the other hand, techniques for the isolation and purification of individual amino acids are known. For example, LeMaster and coworkers published (*Anal. Biochem.*, 122, 238 (1982)) a paper describing the purification of $^2H$ and $^5N$ amino acids. No fewer than five column chromatographic steps were required, and even then these workers were unable to isolate fully labeled cysteine and glutamine, while yields of tryptophan were "erratic." All three of these amino acids are essential for the growth of most mammalian and insect cell lines used as host cells for production of recombinant proteins. Moreover, the procedure utilized piperidine as a prime eluant of the amino acids from the preparative chromatography columns. Piperidine has been reported to be a highly toxic, controlled substance.

The procedures for the purification of the individual amino acids are thus complicated, time-consuming and low-yield and hence are uneconomical. Consequently, while some $^{13}C$ and/or $^{15}N$ amino acids are commercially available, albeit only in small quantities and only on occasion, most are not.

Recently, Fesik and coworkers have described a method for the production of isotopically labeled proteins from mammalian cells for NMR structural studies. (*Biochemistry*, 31, no 51, 12713, (1992)) These workers hydrolyzed both isotopically labeled algal and bacterial proteins with methanesulfonic acid in the presence of tryptamine and imidazole. The purpose of the latter reagents was to serve as "suicide bases" to reduce the destruction of the amino acids tryptophan and histidine respectively. The hydrolysate was then purified by the procedure described by LeMaster and coworkers; namely, by loading the hydrolysate onto a cation exchange column in the H+ form and eluting the amino acids, as a group, from the column with piperidine. The amino acid-containing fractions were combined, evaporated to dryness, redissolved in water, the pH adjusted to 11.5 with sodium hydroxide, and the resulting solution evaporated until the pH remained constant, "indicating that no more ammonia or piperidine was being removed." The amino acids were then filtered through a 500 molecular weight cutoff membrane to remove further impurities and lyophilized. The authors do not indicate whether the resulting amino acids were used directly (i.e. at high pH) or whether the pH of the solution was neutralized, and if so, with which acid. The Fesik et al. work, while representing a technological advance, nevertheless fails to provide a means for universally labeling mammalian cell expressed proteins useful for unambiguous NMR structural determinations. Firstly, the hydrolysis conditions employed destroy asparagine, glutamine and cysteine residues and leave just a "trace" of tryptophan (page 12715, Table 1). Secondly, the procedure employs piperidine as the eluant which is, as noted above, a toxic and controlled substance. Thirdly, LeMaster reports in his original paper that one of the "suicide bases," imidazole co-elutes with the amino acid leucine. LeMaster was able to remove the imidazole by crystallization of leucine. Fesik et al. do not describe such a crystallization step, and indeed, such a step would be impossible in the Fesik et al. procedure where the individual amino acids are not resolved.

Fesik et al. describe the removal of the piperidine eluant by raising the pH of the solution to 11.5 and heat evaporating the solution until the pH remained constant. At this pH, and particularly at the elevated temperatures necessary to remove piperidine (boiling point 106° C.), there is a risk of racemization and/or nucleophilic attack of the amino acids by the piperidine/sodium hydroxide mixture. Such reactions will reduce the amounts of viable amino acids in the mixture, reducing its efficiency as a growth medium. Moreover, as the authors themselves acknowledge, the heat evaporation step is stopped when a stable solution pH indicates "that no more ammonia or piperidine was being removed." It is therefore possible that the mixture of amino acids obtained will contain trace amounts of piperidine, a highly toxic material.

Of more significance however, are the absence of the amino acids asparagine, glutamine and cysteine and the presence of just a "trace" of tryptophan (page 12715, Table 1). Although the lack of asparagine residues was found to be unimportant in the systems investigated by Fesik et al., glutamine was found to be vital for cell growth (page 12716, FIG. 2). The authors provide a method of enzymatically synthesizing glutamine from glutamic acid as a supplement. However, for this reaction to be of value, a source of appropriately labeled glutamic acid has to be available. As the authors note, $^{13}C$, $^{15}N$ labeled glutamic acid is commercially available. However, Triple-labeled glutamic acid, for instance, is not.

By contrast, Fesik provides no method for the preparation of labeled cysteine. Cysteine labeled with a stable isotope has been commercially available only in $^{15}N$-labeled form. Neither double-labeled $^{13}C$, $^{15}N$-cysteine nor triple labeled $^{2}H$, $^{13}C$, N-cysteine have heretofore been available. Consequently, the approach adopted by Fesik and coworkers will not lead to universally labeled products in any case, except for simple $^{15}N$-labeling, as the cysteine and tryptophan residues will not be appropriately labeled. It is possible, moreover, that isotopic leakage of undesired isotope will occur from the incorrectly labeled cysteine residues into other amino acid residues by cellular metabolism.

In principle, the simplest way to produce labeled, including triple-labeled, cysteine, is to culture an organism which is rich in cysteine in the appropriately labeled medium, and to isolate the cysteine from the proteins of that organism. Such organisms will be familiar to those skilled in the art, and include purple sulphur bacteria such as *Rhodopseudomonas speroides* and *capsulata*, other cysteine rich organisms such as *Leptothrix discophora* and *Schizophyllum commune*, and bacteria engineered to produce cysteine rich proteins such as ATCC 31448, an *E. coli* engineered to express human insulin A Chain.

The cysteine would then be isolated from the protein by hydrolysis. However, the only known ways to hydrolyze proteins without concomitant destruction of cysteine are i) hydrolysis under alkaline conditions (See Okuda, *Pr. Acad. Tokyo*, 2, 277) and ii) by enzymatic hydrolysis. Unfortunately, both of these procedures are unsuitable for the production of labeled, and in particular triple-labeled cysteine. Hydrolysis under alkaline conditions can lead to racemization of the required L-cysteine, and also to destruction of several other valuable isotopically labeled amino acids. Enzymatic hydrolysis carries the risk of isotopic contamination from enzyme breakdown products, especially if prolonged hydrolysis times are required, as is usually the case.

As with cysteine, the "trace" amounts of tryptophan present in the mixture employed by Fesik et al. were insufficient for cell growth without supplementation (page 12715, Table 1; page 12716, FIGS. 1 and 2). Although $^{15}N$-labeled tryptophan is commercially available, neither $^{13}C$, $^{15}N$ nor triple-labeled tryptophan is available. Thus for tryptophan to be introduced as a supplement for any labeling experiment other than for simple $^{15}N$-labeling will lead to the same problems associated with the absence of a suitable labeled cysteine residue, namely incomplete isotopic labeling.

Thus, the method provided by Fesik and coworkers will lead to the universal isotopic labeling of proteins only in the case of $^{15}N$-labeled proteins. Although the method is an advance, $^{15}N$-labeled amino acids are already available, as previously indicated. In the case of $^{13}C$, $^{15}N$-labeling experiments, cysteine and tryptophan residues will not be universally labeled, while in the case of $^{2}H$-labeling experiments and triple labeling experiments, cysteine, tryptophan and glutamine residues will be incorrectly labeled.

A further disadvantage of the use of protein hydrolysis procedures for preparing culture media for mammalian cells is that, under hydrolysis conditions, the amino acids, glutamine and asparagine, present in the starting protein, may be converted to glutamic acid and aspartic acid, respectively. Most mammalian cell media contain small quantities of glutamic acid and substantial quantities of glutamine. These media have been developed to produce optimum performance of mammalian cell lines in terms of cell viability and production. Indeed, nearly all mammalian cell lines producing proteins of interest for NMR analysis will have been conditioned in media containing low levels of glutamic acid and high levels of glutamine.

To be applicable for use with the widest possible range of cell lines, therefore, media for the isotopic labeling of mammalian cell proteins advantageously contain small proportions of glutamic acid and larger proportions of glutamine. Similarly, media preferably contain little or no aspartic acid and larger proportions of asparagine.

There is therefore a need for methods to remove the glutamic acid and/or aspartic acid specifically from a mixture of amino acids without altering the proportions of the other amino acids present, convert the thus isolated glutamic acid and/or aspartic acid to the appropriately labeled glutamine and/or asparagine, and supplement the mixture of amino acids with the glutamine and/or asparagine thus obtained.

No procedures for the specific removal of glutamic acid from mixtures of amino acids have been described in the art. Enzymatic techniques for the conversion of glutamic acid to glutamine have been published (Fesik, et al., *Biochemistry*, 31(51), 12713 (1992)). Unfortunately, the reactions are slow (3–4 days) and the accompanying breakdown of the enzyme, leading to contamination with natural abundance amino acids, cannot be ruled out. Moreover, in the case of triple labeled mixtures of amino acids, i.e. those partially labeled with $^{2}H$ as well as universally labeled with $^{13}C$ and $^{15}N$ the presence of the $^{2}H$ atoms would be expected to slow the enzymic conversion of glutamic acid labeled with $^2$H to glutamine still further, due to the isotope effect of $^2$H. Finally, no enzymatic procedure for the conversion of aspartic acid to asparagine has been described in the art.

There has also recently been published a paper by Hsu and Armitage (*Biochemistry*, 31 (51) 12778 (1992)) concerning the NMR determination of the structure of the immunosuppressant drug cyclosporin A bound to its receptor, cyclophilin. These workers labeled cyclophilin, expressed in bacteria, with the NMR inactive isotope $^2$H. They were thus able to examine the structure of the cyclosporin A/cyclophilin complex unencumbered with the signals from the cyclophilin. Given the importance of mammalian ligand/receptor interactions, there is thus also a requirement for mammalian cell proteins, particularly receptors, to be universally labeled with $^2$H. Heretofore, labeled mammalian nutrient media for accomplishing this goal have been unavailable.

Accordingly, for both structure-function studies in general and for rational drug design in particular, there is a need for universally labeled compositions and methods for determining the three-dimensional structures of mammalian cell proteins, and protein complexes. There is consequently a need for producing mammalian cell proteins labeled with a range of stable isotopes in universally labeled form.

SUMMARY OF THE INVENTION

In accordance with the present invention, a method for determining three-dimensional structural information of a protein involves the steps of (a) growing, under protein-producing conditions, a mammalian or insect cell culture which is capable of producing the protein of interest in a nutrient medium which contains all amino acids that are essential for growth of the cells and which contains assimilable sources of carbohydrate, essential minerals and growth factors, wherein the amino acids and any other substrate used by the cells for protein synthesis in such nutrient medium are substantially isotopically labeled with an NMR-active isotope; (b) isolating the labeled protein from the nutrient medium in substantially labeled form and (c) subjecting the protein to NMR spectroscopic analysis to determine information about its three-dimensional structure.

In another aspect of the invention, a method for determining three-dimensional structural information of a protein involves the steps of (a) growing, under protein-producing conditions, a mammalian or insect cell culture which is capable of producing the protein of interest in a nutrient medium which contains all amino acids that are essential for growth of the cell line and which contains assimilable sources of carbohydrate, essential minerals and growth factors, wherein substantially all of the carbon atoms in the amino acids and the carbohydrate source in such nutrient medium are $^{13}$C; (b) isolating the labeled protein from the nutrient medium in substantially labeled form and (c) subjecting the protein to NMR spectroscopic analysis to determine information about its three-dimensional structure.

In yet another aspect of the invention, a method for determining three-dimensional structural information of a protein involves the steps of (a) growing, under protein-producing conditions, a mammalian or insect cell culture which is capable of producing the protein of interest in a nutrient medium which contains all amino acids that are essential for growth of the cell line and which contains assimilable sources of carbohydrate, essential minerals and growth factors, wherein substantially all of the carbon atoms in the amino acids and the carbohydrate source in such nutrient medium are $^{13}$C and substantially all of the nitrogen atoms in the amino acids in such nutrient medium are $^{15}$N; (b) isolating the labeled protein from the nutrient medium in substantially labeled form and (c) subjecting the protein to NMR spectroscopic analysis to determine information about its three dimensional structure.

In a further aspect, this invention is directed to the determination of three-dimensional structural information of a first molecule while complexed with a second molecule, wherein at least one of such molecules is a protein. The procedure involves substantially labeling the first molecule with a stable NMR-active isotope and substantially labeling the second molecule with deuterium, forming a complex between the first and second molecules and subjecting the complex to NMR spectroscopic analysis to determine information about the three-dimensional structure of the first molecule.

Another aspect of the invention involves a novel nutrient medium capable of supporting the growth of a mammalian or insect cell culture, which contains all amino acids that are essential for growth of the cells, an assimilable source of carbohydrate, and essential minerals and growth factors, wherein the amino acids and any other substrate used by the cells for protein synthesis are substantially labeled with $^{13}$C or with both $^{13}$C and $^{15}$N.

In still another embodiment, the invention involves a method for producing a mixture of amino acids in substantially completely isotopically labeled form, which comprises (a) growing a microbial culture in a nutrient medium in which substantially all of the carbon utilized as a substrate for protein biosynthesis is $^{13}$C; (b) recovering a protein fraction from the microbial culture; (c) hydrolyzing the protein under acidic, non-oxidizing conditions in the presence of a sulfhydryl reducing agent to produce a crude mixture of amino acids; (d) subjecting the crude mixture of amino acids to cation exchange chromatography to produce a partially purified mixture of amino acids; (e) subjecting the partially purified mixture of amino acids to anion exchange chromatography to produce a purified mixture of amino acids; and (f) supplementing the purified mixture of amino acids with an amount of $^{13}$C-labeled cysteine sufficient to support protein production by the mammalian or insect cells. The foregoing method may also be used to produce a mixture of $^{13}$C, $^{15}$N-double labeled amino acids or $^2$H, $^{13}$C, $^{15}$N-triple labeled amino acids or to produce a mixture of $^2$H-labeled amino acids.

The invention further provides methods for converting glutamic acid and aspartic acid to glutamine and asparagine respectively and provides isotopically labeled mammalian cell media containing low levels of glutamic acid and enriched with glutamine and culture media optionally containing low levels of or no aspartic acid and enriched for asparagine. In particular, this invention provides methods for specifically removing glutamic acid from the mixture of amino acids produced by the methods described herein and chemically converting the glutamic acid to glutamine. Asparagine can be chemically synthesised from aspartic acid using the same procedures. The efficacy of the procedures is unaffected by the presence of isotopic labels, including $^2$H.

The invention further provides a method for isolating isotopically labeled cysteine from labeled polypeptides and amino acid mixtures. This method may be used to produce cysteine labeled with any combination of $^2$H, $^{13}$C and $^1$N. Amino acid mixtures supplemented with such labeled cysteine are also described.

DESCRIPTION OF THE INVENTION

This invention provides a means for determining three-dimensional structural information about mammalian or insect cell-produced proteins. Since mammalian and insect cells used as hosts for recombinant DNA are capable of producing complex proteins in a form similar or identical to their natural three-dimensional structure, this invention provides a valuable technique for studying the structure-function relationships of biologically active proteins. The procedure involves the growth of mammalian cell lines in a nutrient medium in which all of the amino acids are substantially completely labeled with one or more NMR-active isotopes. The invention allows for the universal labeling of proteins with $^{13}C$ or $^{15}N$ or both and for triple labeling with $^{2}H$, $^{13}C$ and $^{15}N$. The invention further provides for the universal labeling of proteins with $^{2}H$ alone, so as to make them NMR invisible. The latter technique is particularly useful for obtaining structural information for molecules in complexes, such as, for example, hormone-receptor complexes. By making one of the binding partners NMR invisible, the structure of the other binding partner, when labeled with one or more NMR-active isotopes, can be studied.

The mammalian cell line nutrient media of this invention contain isotopically-labeled amino acids derived from microorganisms. Defined nutrient media for mammalian and insect cells are well-known. The growth requirements of these cells are well-understood, and synthetic media containing assimilable sources of carbohydrate, essential minerals and growth factors are commercially available. Some of these media further contain trace amounts of pyruvic acid. When media of this type are desired, it is advantageous to supply the pyruvic acid in appropriately labeled form. Isotopically labeled forms of pyruvic acid are commercially available. Serum-free defined media are commercially available. Serum-free media are preferred for practice of the present invention, so as to facilitate recovery of a relatively pure labeled protein for NMR analysis. Purification of the labeled protein from a serum-free mammalian or insect cell culture medium can be accomplished by any of a variety of known techniques. See, Deutscher, M. P., *Guide to Protein Purifications, Methods in Enzymology*, Vol. 182 (1990).

Universal labeling of proteins is accomplished by supplying all of the essential amino acids and any other substrates used by the cells for protein synthesis in labeled form. As used herein, protein synthesis includes the biosynthesis of carbohydrate side chains in the case of glycoproteins.

The invention provides a simple means of producing a mixture of amino acids. It is easy to perform, is non-hazardous to the user, and is readily scalable, which is important, given that large quantities of labeled media may be required to produce sufficient protein for NMR analysis.

The method of producing the labeled amino acid mixture relies on the fact that amino acids, as a class of compounds, can carry both a positive and a negative charge. They can thus be separated, as a group, both from neutral compounds and from compounds which can carry only a positive or only a negative charge, by absorption on, and elution from, acidic and basic ion exchange resins.

As used herein, an indication that a protein is "substantially labeled" or that "substantially all" of the atoms of a particular element in a molecule are in a given isotopic form means that the molecule is sufficiently enriched with the desired isotope that meaningful NMR spectral information can be obtained. In the case of NMR-active isotopes, such as $^{13}C$ and $^{15}N$, the degree of enrichment will be such that three-dimensional structural information can be deduced from the NMR spectra. In general, about 95% or more of the atoms of a given element will be in the desired isotopic form, preferably greater than about 98%.

In the case of enrichment with $^{2}H$ alone, the degree of enrichment will be such that the labeled molecule does not produce an NMR signal sufficient to interfere with an analysis of an NMR-active species complexed to it. In this case, the level of enrichment is greater than about 70%, with greater than about 95% being particularly preferred.

Alternatively, the level of $^{2}H$ enrichment is such that the signals from the NMR-active nuclei, $^{1}H$, $^{13}C$ as $^{15}N$ are enhanced or better resolved. In general this level of enrichment will range from about 20% to about 100%.

The starting mixture of amino acids is a hydrolysate of a protein, labeled with the stable isotopes of choice. In accordance with the invention, the starting protein is substantially labeled with $^{13}C$, with both $^{13}C$ and $^{15}N$, with $^{13}C$, $^{15}N$ and at least partially with $^{2}H$ or with $^{2}H$ alone. Many techniques have been published to produce such proteins, including growth of bacteria in the presence of labeled carbohydrate and salts (Kay, et al., supra), growth of bacteria in algal lysates (Chubb, R. T., et al., *Biochemistry*, 30, 7718 (1991)), growth of yeast in algal lysates (Powers, R., et al., *Biochemistry*, 31, 4334 (1992)), growth of bacteria and yeast in labeled methanol (See, Moat, A. G. and Foster, J. W., *Microbial Physiology*, 2d Ed., John Wiley & Sons, New York (1988), p. 218) and the phototropic culture of algae in the presence of isotopically labeled $^{13}Co_2$ and/or $^{15}N$ salts (Cox, J., et al., *Stable Isotopes in Pediatric Nutritional and Metabolic Research*, Chapman, T. E. et al., Eds., Intercept Ltd., Andover House, England (1950), p. 1615). Similarly, many procedures for the hydrolysis of proteins have been published, including hydrolysis with hydrochloric acid, methanesulfonic acid (LeMaster, et al., supra) and enzyme hydrolysis. If an enzyme hydrolysis is used then it is convenient to acidify the hydrolysate. This has the advantage of denaturing and precipitating the enzyme, which can then be removed from the hydrolysate by centrifugation.

In the present method, acid hydrolysis is preferred. The acid hydrolysis is advantageously conducted using a strong mineral acid, such as hydrochloric acid, nitric acid or sulfuric acid or a sulfonic acid such as p-toluenesulfonic acid or methanesulfonic acid, the latter being preferred. The acid concentration may vary, depending upon the nature of the protein substrate, but in general is sufficient to effect complete hydrolysis. Typically, acid concentrations range from about 1N to about 6N, preferably from about 2N to about 4N. The acid hydrolysis is carried out under non-oxidizing conditions. These conditions can be achieved by conducting the reaction in vacuo or by purging with an inert gas such as nitrogen, argon or the like.

The protein to be hydrolyzed may be added to the hydrolysis medium at a concentration of between about 0.5 g/10 ml and 5 g/10 ml, preferably at a concentration of between about 1 g/10 ml and 2.3 g/10 ml.

The hydrolysis is conducted at a temperature and for a time sufficient to effect substantially complete hydrolysis, while minimizing racemization or the loss of labile amino acids. The temperature of the hydrolysis generally ranges from about 90° to 140° C., but in order to minimize the racemization of amino acids is preferably in the range 100° to 115° C., with 100° C. particularly preferred. The time of hydrolysis may be in the range of 24 to 72 hours, depending on the protein to be hydrolyzed. Preferably a hydrolysis time of about 48 h is used.

The amino acids that are susceptible to degradation by oxidation are further protected by the presence of a reducing agent. Preferably, a strong sulfhydryl-containing reducing agent is employed, such as thioglycollic acid (Fasman, G.

D., Ed., *Practical Handbook of Biochemistry and Molecular Biology*, CRC, New York (1989), p. 106). The purpose of the reducing agent is not just to protect the vulnerable tryptophan and histidine residues. If thioglycollic acid is used, it can easily be subsequently removed according to the procedure of the invention.

The reducing agent is employed at a concentration in the hydrolysis mixture sufficient to prevent substantial destruction of tryptophan and histidine. For thioglycollic acid, such concentration generally ranges from about 1 to about 7% v/v, preferably from about 3 to about 15% v/v.

The hydrolysate is added to a column of a cation ion exchange resin. The cation exchange resin is preferably in an acid form. In principle, any acid form of resin may be used, but for convenience the resin is in the form of a simple acid such as $H^+$, pyridinium, methylammonium etc. Cation exchange resins that may be used in this method include, Dowex 50X8-400 available from Dow Chemical Co., Midland, Mich. After addition of the hydrolysate to the resin, neutral and acidic contaminants are removed by washing the resin with an acidic solution. In principle, any acid can be used, and for convenience a simple mineral acid such as hydrochloric, sulfuric acid, etc. may be used. The acidic solution has a pH below the pKa of the most acidic amino acid, but not so low as to cause substantial racemization. In general, the pH ranges from about 1 to about 2, preferably about 2. The volume of the acidic solution is sufficient to remove substantially all of the material and acidic contaminants. Elution with about 2–6 bed volumes is usually sufficient.

The acid solution is then removed from the resin by washing the resin column with water. To ensure removal of contaminants the volume of water used is preferably in the range of 2–6 bed volumes.

Following removal of the acid wash with water, the amino acids and the basic materials adhering to the cation exchange resin are eluted with a basic solution. In principle, any basic solution can be used, and advantageously, a simple base such as sodium hydroxide, potassium hydroxide, or a nitrogenous base with the general formula $NR^1R^2R^3$, where $R^1$, $R^2$, and $R^3$ are each independently hydrogen, or $C_1$–$C_4$ alkyl or alkenyl groups, may be used. Examples of such nitrogenous bases include aqueous ammonia, aqueous methylamine, aqueous triethylamine, etc. The basic medium neutralizes the acidic cation exchange resin with concomitant elution of the bound amino acids and basic compounds. The pH of the basic medium is such that the amino groups of the amino acids are neutral while the carboxylate functions of the amino acids are negatively charged. The pH of the basic medium preferably is greater than about 10. To avoid racemization of the amino acids under too strongly basic conditions, the pH advantageously is less than about 13 and preferably is in the range of about 10–11. The basic medium neutralizes the acidic cation exchange resin with concomitant elution of the bound amino acids and basic compounds.

The amino acid mixture may be further purified by anion exchange chromatography. The eluate from the cation exchange column is added to a column of anion exchange resin in a basic form. In principle, any basic form of the resin can be employed, and preferably a simple basic form such as hydroxide is used. Suitable anion exchange resins include Dowex 1X8-100, available from Dow Chemical Co., Midland, Mich. The amino acids are absorbed onto the basic ion exchange resin because, while their amino groups now carry no positive charge, their carboxyl functions are now negatively charged.

The basic and neutral contaminants are removed by washing the resin with a basic solution. The basic solution used in this step may be any of the basic solutions described from the elution of the amino acids from the cation exchange column.

The basic medium is removed from the anion exchange column by elution with water. It is preferred that no basic medium is left in contact with the amino acids bound to the resin, and therefore, about 2–8 bed volumes, preferably at least about 4 bed volumes, of water are used to wash the column.

The amino acids are eluted from the basic anion exchange resin with acid. In principle, any acid solution may be used but for preference, a solution of weak, volatile acid that may be removed by subsequent evaporation is used. Either formic or acetic acid are therefore preferred. The concentration of acid used is such that the pH of the acidic solution is in the range of about 2–6, preferably in the range of about 3–5. The purified amino acids are thus eluted from the column as an off white solution. A further advantage of the invention is that aspartic acid is eluted after all the other amino acids. For instance, all the amino acids except aspartic acid may be eluted from the column with 0.25% v/v aqueous acetic acid. Aspartic acid may then be eluted from the column with 2.5% v/v aqueous acetic acid. A further aspect of the invention is therefore a simple purification of the amino acid aspartic acid. As discussed below, this aspartic acid, which will be in labeled form, may be converted to labeled asparagine, which can then be used to further supplement the mixture of labeled amino acids.

It will be appreciated by those skilled in the art that the above elution procedure is a so-called "step-gradient" elution. It will further be appreciated that a linear, or alternatively an exponential, gradient of concentration of the eluting acid may be used. Such gradients will lead to sequential elution of the amino acids, either as mixtures or as single amino acids depending on the gradient used. A further aspect of the invention is therefore a simple procedure for the purification of amino acids, either singly or as mixtures. Another aspect of the invention is that the amino acids thus isolated may be used to alter the amino acid profile of the overall amino acid mixture. Yet another aspect of the invention is that the overall amino acid mixture can thus be tailored to the requirements of a given cell line.

The isolated amino acids may now be isolated by a standard technique such as evaporation under reduced pressure, or lyophilization. A further aspect of the invention is that the amino acids will be isolated in substantially pure form because the acid eluant used is highly volatile.

A further advantage of the invention relates to the fact that one amino acid, arginine, is much more basic than all the others. It will therefore be eluted last from the cation exchange column, after the other amino acids and after all the contaminants. On elution at a pH in the range of 10–12, arginine will carry no net charge. This is due to the presence of its highly basic guanidinium side chain which will carry a positive charge at pHs in the range 10–12 and which will neutralize the negative charge of the carboxylate function. Unlike all the other amino acids therefore, arginine will pass through the cation exchange resin, after all the contaminants, and can be subsequently isolated and crystallized, for instance as the hydrochloride, by standard techniques (Cox, G. J., *J. Biol. Chem.*, 78, 475 (1928)). A further aspect of the invention is therefore a simple purification of the amino acid arginine.

It will be appreciated by those skilled in the art that the invention, particularly if a sulfhydryl containing reducing agent was used for the hydrolysis step, leads to a mixture of pure amino acids in the same proportion as was in the starting hydrolysate, with little or no variation in yield of each amino acid. A further aspect of the invention is therefore a means of simply preparing a mixture of pure amino acids in the same proportions as in the starting protein. The proportions of the amino acids can therefore be controlled by selecting the appropriate starting protein or mixture of proteins. Alternatively, the mixture of amino acids prepared according to the invention may be supplemented by the addition of an amino acid or acids that are available either commercially or which can be synthesized.

For example, cysteine is an important amino acid in mammalian cell media, yet is not present in high enough concentrations in most bacterial, yeast or algal proteins to support mammalian protein biosynthesis in mammalian on insect cells.

Enzymatic procedures for the synthesis of cysteine are known. For example, U.S. Pat. No. 4,733,011 to Miyahara et al., incorporated herein by reference, discloses a method for preparing L-cysteine from L-serine by enzymatic reaction with hydrogen sulfide. U.S. Pat. No. 4,782,021 to Ishiwata et al., incorporated herein by reference, describes the production of L-serine by reacting lysine and formaldehyde in the presence of serine hydroxymethyltransferase. Isotopically labeled cysteine, including $^{13}$C-cysteine and $^{13}$C, $^{15}$N-cysteine may be prepared by those procedures using commercially available substrates.

The above-described enzymatic methods for making isotopically labeled cysteine are disadvantageous for producing triple-labeled $^2$H, $^{13}$C, $^{15}$N-cysteine, because of the unavailability of suitable triple-labeled starting materials. Even if such substrates were available, deuteration would adversely affect the kinetics of the enzymatic conversion. Accordingly, a further embodiment of this invention involves a novel method for making isotopically labeled cysteine, including triple-labeled cysteine, and amino acid mixtures containing such isotopically labeled cysteine.

In this method, isotopically labeled cysteine, including triple-labeled cysteine, is produced by acid hydrolysis of an appropriately labeled cysteine-containing protein. Cysteine is known to be labile under acid-hydrolysis conditions, the method therefore includes means to i) protect the cysteine during protein hydrolysis, ii) separate the protected cysteine and iii) deprotect and isolate the labeled cysteine.

Chemical protection of thiol groups as S-benzyl ethers has long been known. (For a review see Green, T. and Wats, P. G. M., *Protective Group Chemistry,* 2nd Ed., John Wiley & Sons, New York (1991)) Indeed, cysteine residues are routinely protected with S-benzyl groups during the chemical synthesis of peptides. However, such protected compounds are not very acid stable, and are also destroyed by the conditions used to hydrolyze proteins.

It has now been found that the thiol group is stable in strong, hot acidic media capable of hydrolyzing proteins when protected as the charged benzyl thioether of the formula

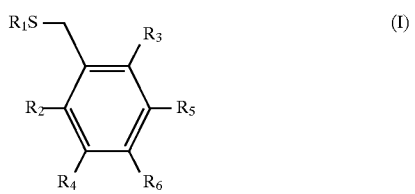

wherein $R_1$ is the cysteine residue, either alone or as part of a protein molecule, and at least one of $R_2$–$R_6$ is either an acidic group, such as carboxy, $C_1$–$C_4$ carboxyalkyl or $C_1$–$C_4$ carboxyalkoxy or a basic group such $C_2$–$C_4$ dialkylamino, $C_3$–$C_6$ dialkylaminoalkyl or $C_3$–$C_6$ dialkylaminoalkoxy, and the remaining $R_2$–$R_6$ groups are either singly or in combination, hydrogen, halogen, $C_1$–$C_6$ alkyl or $C_1$–$C_6$ alkoxy. Preferably, $R_6$ is an acidic group such as carboxy, carboxymethyl or carboxymethoxy, or a basic group such dimethylamino, dimethylaminomethyl or dimethylaminomethoxy, and the remaining groups $R_2$–$R_5$ are either singly or in combination, hydrogen, halogen, $C_1$–$C_6$ alkyl or $C_1$–$C_6$ alkoxy.

Compound (I) may be prepared in high yield by treating the cysteine thiol (II) with a halobenzyl compound (III)

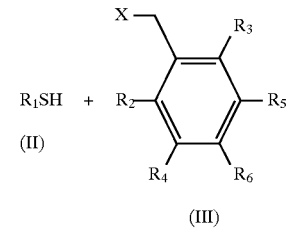

wherein X is halogen, preferably chloro or bromo and $R_1$–$R_6$ are defined as above, in a basic medium, such as dilute ammonia or aqueous sodium hydroxide.

The presence of the charged acid or basic group in (I) enhances the stability of the benzyl thioether in acid media such that the starting thiol is protected under hot acid conditions, and also provides a basis for separating the protected molecule from other molecular species by means of differential solubilities, ion exchange chromatography and the like.

The thiol derivative (I) can be reconverted to the starting thiol (II) by known techniques, such as with treatment with an alkali metal, for instance sodium in liquid ammonia or ethanol.

In a preferred aspect of the invention, cysteine (II) is protected as the acidic P-carboxybenzyl thioether (IV)

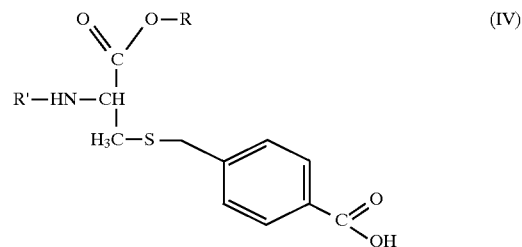

wherein R and R' are each hydrogen when the starting material for the reaction is free cysteine or R and R' represent the adjacent amino acid residues in the polypeptide when the starting material is a polypeptide.

Compound (IV) may be prepared in high yield by treating cysteine (II), either as the free amino acid or as a peptide residue in a polypeptide, with the p-chloromethylbenzoic acid in a mildly basic medium such as dilute aqueous ammonia or aqueous sodium hydroxide. For the preparation of isotopically labeled cysteine, an appropriately isotopically labeled protein is treated with (III) in the presence of dilute aqueous ammonia or aqueous sodium hydroxide under thiol ether-forming conditions. Suitable proteins will be known by those skilled in the art, but those derived from purple sulphur bacteria such as *Rhodopseudomonas speroides* and *capsulata,* other cysteine rich organisms such as *Leptothrix discophora* and *Schizophyllum commune,* and bacteria engineered to produce cysteine rich proteins such as ATCC 31448, an *E. coli* engineered to express human insulin A chain, said organisms having been grown in appropriately labeled media, are particularly preferred.

The cysteine derivative (IV) is stable in hot, strongly acidic media, while less soluble in acid and neutral media at room temperature. Compound (IV) is consequently easily separated from the other amino acids in a protein hydrolysate, for instance by filtration or by centrifugation of the cooled hydrolysate. By contrast, the cysteine derivative (IV) is highly soluble in basic organic solvents, such as ethanolic ammonia and can thus be separated from the other components of a protein hydrolysis by basic organic extraction with solvents such as aqueous ethanolic ammonia.

Alternatively, the cysteine derivative (IV) can be isolated from a protein hydrolysate by a variation of the amino acid purification process described above. The protein hydrolysate is absorbed onto an ion exchange resin in the H+ form and contaminants removed by elution with acid. Following a water wash, the amino acids of the hydrolysate, including the cysteine derivative (IV), are eluted from the H+ resin and onto a OH⁻ resin by elution with ammonia. Following a water wash, the amino acids are eluted from the OH⁻ resin by elution with dilute acetic acid. However, the cysteine derivative (IV) is more acidic than the other amino acids due to the presence of the benzoic acid side chain and consequently is eluted after all the other amino acids including aspartic acid. The cysteine derivative (IV) is then isolated either by drying of the appropriate fractions or by concentration on an H⁻ resin and subsequent elution with dilute ammonia and evaporation of the appropriate fractions.

The cysteine derivative (IV) can easily be reconverted back to cysteine (II) by standard techniques, preferably treatment with an alkali metal in a suitable solvent, for instance sodium in liquid ammonia or ethanol.

Cysteine can be produced in unlabeled, single-labeled, double-labeled or triple-labeled form by the above procedure. The desired isotopic composition of the cysteine-containing protein starting material can be controlled by controlling the composition of the nutrient medium used for producing the protein.

It will be appreciated by those skilled in the art that mammalian cell media contain, in addition to amino acids and glucose, various compounds such as vitamins, fatty acids, essential minerals and growth factors. A further aspect of the invention is that the mixture of pure labeled amino acids produced by the invention may be added to any mixture of growth factors tailored for a given cell line, thereby producing an isotopically labeled medium for any mammalian or insect cell line. In addition to isotopically labeled amino acids, other substrates utilized by the cells for protein synthesis may be provided in labeled form. For example, carbohydrate, such as glucose, can be provided in the $^{13}$C-labeled form and/or in deuterated form.

It will be further appreciated by those skilled in the art that protein hydrolysis procedures destroy the amino acids asparagine and glutamine, with concomitant formation of the acidic amino acids aspartic and glutamic acid respectively. Most mammalian cell media contain large quantities of glutamine. Unexpectedly, addition of glutamine to the mixture of amino acids produced by this invention is not required for optimization of the growth rate or recombinant protein productivity of certain mammalian cells. However, glutamine supplementation has been found to be important in obtaining optimum performance of some mammalian and insect cell lines. A further aspect of the invention is that the mixture of amino acids produced by the invention may or may not be supplemented with glutamine depending upon the characteristics of the particular cell line with which the medium is to be used. It has been found that when the preferred conditions described here are used, no detectable racemization occurs.

It has been found that glutamic acid can conveniently be separated from the amino acid mixture by a further chromatography step and then converted to glutamine by a chemical or enzymatic procedure. The glutamine so produced can then be used to supplement the amino acid mixture as required.

At neutral pH only the glutamic acid residues in the amino acid mixture will carry a net negative charge, due to the presence of two carboxylate groups and one amino function. All the other amino acids will either carry no overall charge (e.g. glycine) or a net positive charge (e.g. lysine) at neutral pH.

Thus, glutamic acid can be specifically separated from the amino acid mixture following removal of the eluting acid, e.g. by lyophilization, by passage of the mixture through an anion exchange resin prepared with a weak acid. In principle, any weak acid would be suitable but for preference the anion exchange resin is in the acetate or formate form.

The glutamic acid, by virtue of its net negative charge will adhere to the anion exchange resin, while the neutral or positively charged amino acids will pass through. When the amino acids have eluted from the resin, the resin may be washed with water and the glutamic acid eluted from the column with a solution of an appropriate acid. The glutamic acid thus isolated can be recovered by a standard technique such as evaporation under reduced pressure or lyophilization.

The glutamic acid may then be converted to glutamine by known procedures, such as the enzymatic procedure described by Fesik et al. However, as noted above, the enzmatic procedure is disadvantageous for deuterated and triple-labeled substrates. Alternatively, in accordance with the present invention, the novel chemical procedure outlined in Scheme 1 below may be used.

Scheme 1

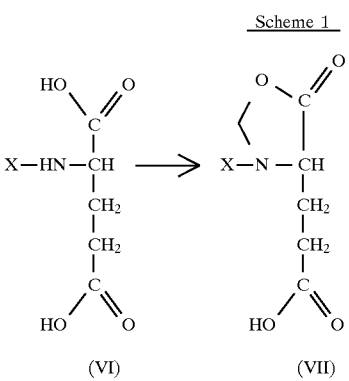

(VI)   (VII)

-continued
Scheme 1

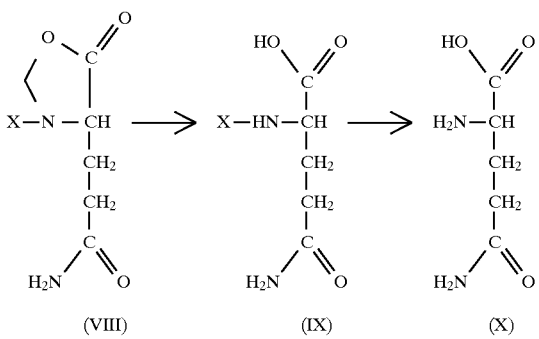

(VIII)  (IX)  (X)

The glutamic acid is first protected at the amino function to give (VI). Many suitable protecting groups will be known to those skilled in the art, and include Fmoc, t-Boc and the like.

The N-protected glutamic acid is then cyclized to produce the oxazolidinone (VII). Techniques for this transformation are known by those skilled in the art, e.g., see, Itoh (*Chem. Pharm. Bull*, 17, 1679, 1969)). In the Itoh procedure, Compound (VI) is treated with trioxane in the presence of catalytic amounts of a strong acid, such as toluenesulfonic acid, to give (VII) which can be isolated by known techniques. The free carboxylic acid group of (VII) is then activated by a suitable activating agent, such as dicyclohexylcarbodiimide, diisopropyl carbodiimide, n-bromosuccinimide and the like. Additional activating groups will be known to those skilled in the art.

The activated oxazolidinone is then treated with ammonia gas to give the cyclic amide derivative (VIII). When preparing $^{15}$N-labeled glutamine, the ammonia will also be required to be labeled with $^{15}$N. Like all $^{15}$N materials, $^{15}$N-ammonia is expensive. Moreover, being a gas it is also difficult to control and measure accurately. For preference therefore the $^{15}$N-ammonia gas is generated by treating, in a separate flask, a solution of an $^{15}$N salt, such as $^{15}$N-ammonium chloride, $^{15}$N-ammonium sulfate, etc. with a base, and bubbling the evolved ammonia through the solution of the activated oxazolidinone. Suitable solvents include polar, aprotic organic solvents, such dimethylsulfoxide and dimethylformamide, while suitable bases include strong or moderately strong miscible bases, such as tetramethylguanidine and sodium hydride.

The cyclic amide derivative (VIII) is then hydrolyzed with a weak aqueous base in a suitable solvent to give the N-protected glutamine derivative (IX). Many such bases are available, but for simplicity the base employed is a simple alkali such as sodium hydroxide in aqueous ethanol. In order to minimize concommitant hydrolysis of the amide function, only 1–5 equivalents of base are preferably employed with 1–2 equivalents being most preferred.

The resulting N-protected glutamine is then deprotected by known procedures depending upon the particular protecting group used. (See Green, et al., supra.) The glutamine (X) may be isolated, e.g., by crystallization or evaporation under reduced pressure, and may be purified, e.g., by known chromatographic procedures.

It will be appreciated by those skilled in the art that the above procedure may also be used to convert aspartic acid to asparagine. Another aspect of the invention is a method for the production of asparagine.

The above-described hydrolysis conditions, coupled with the procedures for preparing labeled cysteine glutamine and asparagine, enable the preparation of a mixture of amino acids labeled with any combination of $^2$H, $^{13}$C and 15N. A further aspect of the invention is that amino acids of any isotopic substitution can be purified by the process of the invention. Because the invention relies on the protonation of the amino and carboxylic functions of the amino acids only, amino acid mixtures of any isotopic labeling can be purified by the invention.

Whatever the isotopic labeling, the resulting mixture of amino acids is sufficient to support the growth of mammalian or insect cells. Yet another aspect of the invention is that the resulting mammalian or insect cells and their metabolic products will be universally labeled with the same isotopic mixture as the starting material.

The invention is illustrated by the following examples, which are included by way of illustration only and in no way restrict the scope of the invention.

EXAMPLES

Example 1

An algal biomass (500 g) from a culture of Chlorela sp was diluted (H$_2$O) to approx 10% slurry, placed in ice, and the cells broken by three passages through a Microfluidizer. The resulting slurry was centrifuged at 5,000 rpm for 15 mins. at 5° C. The supernatant was collected, and the pellet resuspended in H$_2$O and recentrifuged under the same conditions. This process was repeated twice. The supernatants were combined, treated with trichloracetic acid (final concentration 5% v/v) and the whole stored at 5° C. overnight.

The resulting suspension was centrifuged at 5,000 rpm at 5° C. for 30 mins. The supernatant was decanted, the pellet resuspended in an equal volume of acetone, and the whole centrifuged at 5,000 rpm at 5° C. for 15 mins. The supernatant was removed, the pellet suspended in 500 ml of ethanol/ether and collected by filtration under reduced pressure. The pellet was washed with ethanol/ether and dried under reduced pressure.

Seven grams of a soluble protein fraction described above was heated in vacuo in 3M methanesulfonic acid (70 ml) containing 4% v/v thioglycollate for 48 h at 100° C. On cooling, the hydrolysate was slowly poured onto water (70 ml) cooled in an ice bath and the resulting mixture left to stand for approx. 10 min. The resulting cooled solution was centrifuged (RC-3B, 250 ml bucket, 5,000 rpm, 10 min.). The supernatant was pumped (36 ml/min.) onto a column of Dowex 50X8 ion exchange resin (H+ form, 500 g) equipped with an FMI Lab Pump QSY at its base.

When all the hydrolysate had been pumped onto the column, dilute aqueous H$_2$SO$_4$ (pH2.0, 1.15 L] followed by H$_2$O (2 L) were pumped (36 ml/min.) throughout the column. Fractions (labeled H+, 500 ml) were collected from the bottom of the column.

The H+ column was then connected via the pump to a column of Dowex 1X8-100 ion exchange resin (OH— form, 500 g). Dilute aqueous ammonia (1% v/v, 9 L) was pumped (36 ml/min.) through the H+ column and the effluent carried throughout to the OH$^-$ column. Fractions (labeled OH$^-$, 500 ml) were now collected from the base of the OH$^-$ column.

TLC analysis (Analtech Silica GS plates, n-BuOH:AcOH:H$_2$O (2:1:1 v/v), developer:ninhydrin (1% v/v in MeOH:Glac AcOH (97:3 v/v)) revealed the presence of arginine in fractions OH-13-18.

After elution of the arginine fractions, the pump was stopped and connected directly to the OH$^-$ column. The pump was restarted while fractions (500 ml) continued to be collected from the OH⁻ column.

Dilute aqueous acetic acid (0.25% v/v, 10 L) was then pumped through the OH⁻ column while 500 ml fractions continued to be collected from the base of the column. Pumping continued until no further ninhydrin-positive spots were detected in the effluent.

TLC analysis (Analtech Silica GS plates, n-BuOH:AcOH:H$_2$O (2:1:1 v/v)), developer:ninhydrin (1% v/v in MeOH:Glac AcOH (97:3 v/v)) revealed the presence of mixed amino acids (fractions OH-25-36).

The arginine containing fractions and the mixed amino acid fractions were independently dried and concentrated by freeze drying. The residues were dissolved in water, filtered through 0.22 micron filters into sterile bottles and re-freeze dried. The arginine fraction was crystallized as the hydrochloride essentially according to the procedure described in Cox, J., supra, yield 0.31 g. The mixed amino acid fractions were isolated as a pale yellow powder, yield 4.6 g.

Example 2

CHO-SSFM-1 media (Gibco), a serum-free medium optimized for CHO cells, was obtained from the suppliers with the amino acids omitted. Two media samples were prepared as follows:

To 200 ml of amino-acids-free CHO-SSFM-1 aliquots were added
1. Mixed amino acids (340 mg)+cysteine(20 mg)+ crystallized arginine(40 mg)
2. Mixed amino acids (340 mg)+cysteine(20 mg)+ crystallized arginine(40 mg)+glutamine(120 mg).

The solutions were sterilized by passage through 0.22 micron filters and aliquots (2–3 ml) were inoculated with CHO cells (initial concentration 1×10⁵/ml). Cell counts and % viable cells (%) were recorded relative to a sample of control CHO-SSFM-1 media.

|         | 48 h    | 72 h    | 96 h    | 120 h    | 144 h   | 168 h   |
|---------|---------|---------|---------|----------|---------|---------|
| Control | 2.4(99) | 5.2(96) | 7.0(93) | 7.0(91)  | 5.6(83) | 4.0(64) |
| 1       | 1.6(99) | 3.8(93) | 5.1(97) | 12.0(92) | 8.2(84) | 5.0(72) |
| 2       | 2.2(99) | 4.0(95) | 5.5(93) | 7.2(95)  | 7.2(82) | 7.0(69) |

These results indicate that i) that the amino acid mixture obtained by the method of this Example gave growth characteristics indistinguishable from that of the control and ii) that the addition of glutamine was not necessary for cell growth.

Example 3

Double-labeled amino acids were prepared substantially by the method described in Example 1, except that the algal biomass used was derived from a culture of the Chlorela sp. grown utilizing $^{13}CO_2$ and $K^{15}NO_3$ as the sole carbon and nitrogen sources respectively. $^{13}C$, $^{15}N$-Cysteine was prepared by the enzymatic procedure substantially as described above.

CHO-SSFM-1 medium (Gibco) was also obtained from the suppliers with the amino acids, carbohydrate, intermediate metabolites and protein hydrolysate omitted.

To 1 liter of this medium were added:
$^{13}C$, $^{15}N$-Mixed amino acids (including $^{13}C$, $^{15}N$-glutamic acid): 3 g
$^{13}C$, $^{15}N$-Arginine-HCl: 240 mg.
$^{13}C$, $^{15}N$-Cysteine: 160 mg
$^{13}C$-Sodium pyruvate (Isotec Inc.): 70 mg
$^{13}C$-D-Glucose: 3.8 g.

The resulting solution was sterilized by passage through 0.22 micron filters. 250 ml of this solution was innoculated with a CHO cell line engineered to express and secrete human choriogonadotrophin (hCG) to a final concentration of 3×10⁶ cells/ml. The culture was stirred for 15 hours, whereupon the cells were isolated by centrifugation. The cell pellet was resuspended in 500 ml of the $^{13}C$, $^{15}N$-labeled medium prepared as above to a concentation of 1.2×10⁶ cells/ml and the whole stirred for 73 hours. A control culture using commercially available CHO-SSFM-1 was run according to the same regime.

The concentration of $^{13}C$ and $^{15}N$-labeled hCG was then determined by RIA using an antibody directed at hCG. The concentration of $^{13}C$, $^{15}N$-labeled hCG was found to be 90 pmole/ml at 73 h. compared with a control concentration at unlabeled hCG in the control culture of 100 pmole ml at 88 hr.

Example 4

Preparation of Ammonium cysteine-S-4-methylbenzoate

Cysteine (2.42 g, 20 mmol) and 4-chloromethylbenzoic acid (3.74 g, 2 mmol) were suspended in H$_2$O (90 ml) and the suspension treated with concentrated aqueous ammonia. The resulting solution was stirred at room temperature for 1 hr. Approximately 50 ml of the solvent was then removed by evaporation, whereupon a precipitate appeared. Concentrated aqueous ammonia was then added dropwise until the precipitate had dissolved. Further solvent was removed by evaporation until a precipitate started to form. Dry distilled ethanol was then added dropwise and ammonium cysteine-S-4-methylbenzoate was obtained as white crystals (Found: C, 49.0: H, 5.8; N, 9.3; S, 11.6 C$_{11}$H$_{16}$N$_2$O$_4$S theoret. C, 48.5 H, 5.9; N, 10.3; S, 11.8); yield 4.9 g (90%), Rf (2:1:1 v/v/v n-BuOH:H$_2$O:AcOH) 9.73. Delta H (D$_2$O, 300 Mhz) 7.76 (2H, d, J 8 Hz), 7.37 (2H, d, J 8 Hz), 3.78 (2H, s), 3.73 (1H, dd, J2, 5 Hz), 2.90 (2H, m). Delta C (D$_2$O, 75 Mhz) 175.30, 172.89, 141.18, 135.43, 129.34, 128.86, 53.60, 35.178, 31.78, 28.16.

Example 5

Stability of Ammonium cysteine-S-4-methylbenzoate to acid hydrolysis conditions

Ammonium cysteine-S-4-methylbenzoate (1 g) was added to a frozen aqueous solution (10 ml) of methanesulfonic acid (3M) and thioglycollic acid (4%) in a Schlenk tube. Air was removed by a vacuum pump, the tube sealed and the whole was heated to 100° C. for 48 hours. The suspension was then cooled, and ammonium cysteine-S-4-methylbenzoate was isolated by centrifugation and washing with water (3×50 ml) in quantitative yield.

Example 6

Isolation of Cysteine from Ammonium cysteine-S-4-methylbenzoate

Ammonium cysteine-S-4-methylbenzoate (200 mg, 0.76 mmol) was added to a two-neck pear shaped flask. The flask was cooled in a dry ice/acetone bath and flushed with ammonia gas. When approximately 10 ml of ammonia liquid had condensed, sodium metal (approximately 50 mg) was added at 1 minute intervals until a permanent indigo color was obtained. dry ice (approximately 100 mg) was then immediately added, whereupon a white precipitate formed. The ammonia was allowed to evaporate, and the residue treated with further dry ice. When all the ammonia had evaporated, water (10 ml) was added and the pH adjusted to approximately 8 by careful addition of with concentrated hydrochloric acid. Air was blown through the mixture for 24 hours, the pH adjusted to approximately pH 5 by further addition of concentrated hydrochloric acid, and the suspension stirred. The resulting precipitate was collected by filtration, suspended in degassed water (approx 10 ml), treated with dithiothreitol (114 mg) and the whole stirred at 50° C. for 2 hours under nitrogen. The resulting suspension was filtered through Whatman No. 1 paper, and evaporated to a gum. Dropwise addition of dry distilled ethanol provided cysteine as white platelets in 2 crops, yield 30 mg.

Example 7

Isolation of Cysteine from Lysozyme

Lysozyme (log) was dissolved in water (1 L), treated with trichloroacetic acid (50 g) and stood at 40° C. overnight. The resulting precipitate was isolated by centrifugation, washed with acetone (300 ml, x3) and dried. Yield 9.95 g.

The denatured lysozyme was suspended in degassed water under an atmosphere of nitrogen and treated with dithiothreitol (2.14 g). The resulting mixture was shaken at room temperature overnight.

Dry distilled ethanol (200 ml) was added and the solution centrifuged at 15 k for 10 minutes. The pellet was resuspended in ethanol (200 ml) and recentrifuged. This last operation was repeated.

4-Chloromethylbenzoic acid (1.54 g) was dissolved in degassed water (42 ml) and concentrated ammonia (7 ml). The resulting solution was added to the pellet isolated above, and the whole shaken at room temperature under nitrogen overnight.

Dry distilled ethanol (200 ml) was added and the solution centrifuged at 5 k for 10 minutes. The pellet was resuspended in ethanol (200 ml) and recentrifuged. This last operation was repeated. The pellet thus obtained was isolated by drying in a desiccator.

The ethanol washes obtained above were found to contain proteinaceous material. Therefore, the combined supernatants obtained above were centrifuged at 15 k for 10 minutes and the pellet isolated. Degassed water (50 ml) and dithiothreitol were added and the whole shaken under nitrogen at room temperature overnight. Acetone (100 ml) was added and the whole centrifuged at 5 k for 10 minutes.

The pellet was dissolved in degassed water (125 ml) and treated with a solution of 4-chloromethylbenzoic acid (0.77 g) dissolved in water (21 ml) and concentrated aqueous ammonia (4 ml). The whole was shaken under nitrogen at room temperature overnight. Acetone (100 ml) was added and the whole centrifuged at 4 k for 10 minutes. The pellet thus obtained was dried in a desiccator and combined with the pellet obtained earlier. Total yield, 9.5 g (87% based on lysozyme amino acid sequence).

The resulting protein fraction (9.5 g) was heated in vacuo in 3M methanesulfonic acid (95 ml) containing 4% v/v thioglycollate for 48 hours at 100° C. On cooling, the hydrolysate was mixed with water (95 ml) and the resulting mixture pumped (50 ml/min) on to a column of Dowex 1X2-400 ion exchange resin (H+ form, 250 g) equipped with an FMl Lab Pump QSY at its base.

When all of the hydrolysate had been pumped onto the column, dilute aqueous $H_2SO_4$ (pH2.0, 1 L) followed by $H_2O$ (1.25 L) were pumped (50 ml/min) through the column. The $H^+$ column was then connected via the pump to a column of Dowex 50X8-100 ion exchange resin ($OH^-$ form, 250 g) Dilute aqueous ammonia (2% v/v, 6 L) was pumped (50 ml/min) through the $H^+$ column and the effluent carried through to the $OH^-$ column. Fractions (2 L) were collected form the base of the $OH^-$ column.

Tlc analysis (Analtech Silica GS plates, n-BuOH:AcOH:$H_2O$ (2:1:1 v/v), developer ninhydrin (1% v/v in MeOH:Glac AcOH (97:3 v/v) revealed the presence of arginine in fractions 2 and 3.

After elution of the arginine fractions, the pump was stopped and connected directly to the $OH^-$ column, which was eluted with water (2 L). The pump restarted while fractions (2 L) continued to be collected form the $OH^-$ column.

Dilute aqueous acetic acid (0.25% v/v, 10 L) was then pumped through the $OH^-$ column while 500 ml fractions continued to be collected form the base of the column. Pumping continued until no further ninhydrin-positive spots were detected in the effluent.

Tlc analysis (Analtech Silica GS plates, n-BuOH:AcOH:$H_2O$ (2:1:1 v/v), developer ninhydrin (1% v/v in MeOH:Glac AcOH (97:3 v/v) revealed the presence of mixed amino acids (fractions 11, 12, and 13).

Dilute aqueous acetic acid (2.5% v/v, 12 L) was then pumped through the $OH^-$ column while 1 L fractions were collected form the base of the column. Pumping continued until no further ninhydrin-positive spots were detected in the effluent.

Tlc analysis (Analgech Silica GS plates, n-BuOH:AcOH:$H_2O$ (2:1:1 v/v), developer ninhydrin (1% v/v in MeOH:Glac AcOH (97:3 v/v) revealed the presence of aspartic acid (fractions 15–18) and cysteine-S-4-methylbenzoic acid) (fractions 18–25).

The cysteine-S-4-methylbenzoic acid containing fractions were combined and the pH was adjusted to 2 with dilute sulphuric acid. The resulting solution was passed through a Dowex 1X2-400 ion exchange resin ($H^+$ form, 25 g) at 25 ml/min. When all rolysate had been pumped onto the column, dilute aqueous $H_2SO_4$ (pH 2.0, 500 ml) followed by $H_2O$ (500 ml) were pumped through the column.

Dilute aqueous ammonia (2% v/v, XXL) was pumped 25 ml/min) through the column. Fractions (approx 150 ml) were collected from the base of the $OH^-$ column.

Tlc analysis (Analtech Silica GS plates, n-BuOH:AcOH:$H_2O$ (2:1:1 v/v), developer ninhydrin (1% v/v in MeOH:Glac AcOH (97:3 v/v) revealed the presence of ammonium cysteine-S-(4-methylbenzoate) in fraction 12 which was evaporated to yield ammonium cysteine-S-(4-methylbenzoate) as a white powder, yield 0.47 g (32% based on derivatized lysozyme).

Example 8

Isolation of Ammonium (50% $^2H$, $^{13}C$, $^{15}N$-labeled cysteine)-S-4-methylbenzoate 10 g of the 50% $^2H$, $^{13}C$, $^{15}N$-labeled mixed amino acids containing glutamic acid (prepared as in Example 9) were dissolved in 436.2 ml $H_2O$ and 436.2 ml $D_2O$ containing $^{15}NH_4CL$ (8 g), NaCl (5 g), phosphate buffer (pH 7, 100 ml), TK-M Metal Salts (20 ml), calcium chloride (concentrate, 4 ml), vitamin mix (1.4 ml), riboflavin (2 ml), p-aminobenzoic acid (0.2 ml). The resulting solution was filter sterilized and divided into equal portions in two 500 ml shake flasks. The solutions were inoculated with a culture of ATCC 31448 (an *E. coli* engineered to express human insulin A chain), and shaken at 37° C. for 24 hours.

The culture was then centrifuged and the cell pellet isolated by freeze drying to yield approximately 1.1 g dry matter.

The cell pellet was then treated sequentially with dithiothreitol and 4-chloromethylbenzoic acid, and hydrolyzed according to the techniques described in Example 7. The resulting derivatized biomass was purified according to the techniques of Example 7 except that 25 g of Dowex 1X2-400 ion exchange resin ($H^+$ form) and Dowex 50X8-100 ion exchange resin ($OH^-$ form) were employed. The eluted fractions containing ammonium (50% $^2H$, $^{13}C$, $^{15}N$-labeled-cysteine)-S-4-methylbenzoate were combined and the pH was adjusted to 2 with dilute sulphuric acid. The resulting solution was passed through a Dowex 1X2-400 ion exchange resin ($H^+$ form, 5 g) at 10 ml/min. When all the hydrolysate had been pumped onto the column, dilute aqueous $H_2SO_4$ (pH2.0, 200 ml) followed by $H_2O$ (100 ml) were pumped through the column.

Dilute aqueous ammonia (2% v/v, 1 L) was pumped (10 ml/min) through the column. Fractions (approx 15 ml) were collected form the base at the $OH^-$ column. Tlc analysis (Analtech Silica GS plates, n-BuOH:AcOH:$H_2O$ (2:1:1 v/v), developer ninhydrin (1% v/v in MeOH:Glac ACOH (97:3 v/v) revealed the presence of a component of identical Rf to ammonium cysteine-S-(4-methylbenzoate) prepared in Example 1. The appropriate fractions were evaporated to yield ammonium (50% $^2H$, $^{13}C$, $^{15}N$-labeled-cysteine)-S-(4-methylbenzoate) as a white powder, yield 30 mg.

Example 9

A culture of Chlorella sp was grown in a solution of 1:1 v/v $H_2O/D_2O$ in the presence of >98% $^{13}CO_2$ and >98% $K^{15}NO_3$ as the sole carbon and nitrogen sources respectively. The resulting algal biomass (approximately 500 g) was diluted ($H_2O$) to approx 10% slurry, placed in ice, and the cells broken by three passages through a homogenizer. The resulting slurry was centrifuged at 5,000 rpm for 25 min at 5° C. The supernatant was collected, and the pellet resuspended in $H_2O$ and recentrifuged under the same conditions. This process was repeated twice. The supernatants were combined, treated with trichloracetic acid (final concentration 5% v/v) and the whole stored at 5° C. overnight.

The resulting suspension was centrifuged at 5,000 rpm at 5° C. for 30 minutes. The supernatant was decanted, the pellet resuspended in an equal volume of acetone, and the whole centrifuged at 5,000 rpm at 5° C. for 15 minutes. The pellet suspended in 500 ml of ethanol/ether and dried under reduced pressure. 52 g of the resulting 50% $^{H2}$, $^{13}C$, $^{15}N$-labeled protein was heated in vacuo in 3M methanesulfonic acid (520 ml) containing 4% v/v thioglycollate for 48 hours at 100° C. On cooling, the hydrolysate was slowly poured onto water (520 ml) cooled in an ice bath and the resulting mixture left to stand for approx 10 min. The resulting cooled solution was centrifuged (RC-3B, 250 ml bucket, 5 k, 10 min). The supernatant was pumped (200 ml/min) on to a column of Dowex 1X2-400 ion exchange resin ($H^+$ form, 2.5 Kg) equipped with an FMl Lab Pump Model QD at its base.

When all the hydrolysate had been pumped ont the column, dilute aqueous $H_2SO_4$ (pH2.0. 7.5 L) followed by $H_2O$ (11 L) were pumped (200 ml/min) through the column.

The $H^+$ column was then connected via the pump to a column of Dowex 50X8-100 ion exchange resin ($OH^-$ form, 2.5 Kg). Dilute aqueous ammonia (2 % v/v, 50 L) was pumped (200 ml/min) through the $H^+$ column and the effluent carried through to the $OH^-$ column. Fractions (2 L) were now collected from the base of the $OH^-$ column.

Tlc analysis (Analtech Silica GS plates, n-BuOH:AcOH:$H_2O$ (2:1:1 v/v), developer ninhydrin (1% v/v in MeOH:Glac AcOH (97:3 v/v) revealed the presence of 50% $^2H$, $^{13}C$, $^{15}N$-labeled arginine in fractions 11–24.

After elution of the arginine fractions, the pump was stopped and connected directly to the $OH^-$ column. The pump was restarted and water (14 L) pumped through the $OH^-$ column. Fractions (2 L) continued to be collected.

Dilute aqueous acetic acid (0.25 % v/v) was then pumped through the $OH^-$ column while 2 L fractions continued to be collected from the base of the column. Pumping continued until no further ninhydrin-positive spots were detected in the effluent.

TLc analysis (Analtech Silica GS plates, n-BuOH:AcOH:$H_2O$ (2:1:1 v/v), developer ninhydrin (1% v/v in MeOH:Glac AcOH (97:3 v/v) revealed the presence of 50% $^2H$, $^{13}C$, $^{15}N$-labeled mixed amino acids (including) 50% $^2H$, $^{13}C$, $^{15}$-labeled glutamic acid) in fractions 46–58. The 50% $^2H$, $^{13}C$, $^{15}N$-labeled mixed amino acids were isolated as a pale yellow powder by lyophilization.

The 50% $^2H$, $^{13}C$, $^{15}N$-labeled mixed amino acids isolated above were dissolved in water (8 L) and pumped (50 ml/min) through a column of Dowex 50X8-100 ion exchange resin (acetate-form, 500 g). Fractions (2 L) were collected. When all the mixed amino acid solution had been added to column, water was pumped through the column until ail of the amino acids had been eluted.

Tlc analysis (Analtech Silica GS plates, n-BuOH:AcOH:$H_2O$ (2:1:1 v/v), developer ninhydrin (1 v/v in MeOH:Glac AcOH (97:3 v/v) revealed the presence of 50% $^2H$, $^{13}C$, $^{15}N$-labeled mixed amino acids (minus 50% $^2H$, $^{13}C$, $^{15}$-labeled glutamic acid) in fractions 1–6 which were isolated as a pale yellow powder by lyophilization. Yield, 20.63 g.

The column was then washed with dilute acetic acid (3%, 6 L), 50% $^2H$, $^{13}C$, $^{15}N$-labeled glutamic acid was eluted as the sole amino acid component in fractions 7–8, and was isolated as a white powder by lyophilization.

Yield, 2.9 g. DeltaH ($D_2O$, 300 MHz) Broad multiplicities due to $^{13}C$, $^{15}N$ and $^2H$ coupling at 4.19, 3.97, 3.72, 3.48, 3.11, 2.68, 2.26, 2.07 and 1.83. Delta C ($D_2O$, 75 MHz) 177.30 (d), 173.92 (q), 54.20 (d), 53.49 (d), 51.58–50.37 (m), 35.50–34.28 (m), 30.36 (d), 29.64 (d), and 25.92–24.99 (m).

The 50% $^2H$, $^{13}C$, $^{15}N$-labeled amino acid mixtures were exampled by HPLC (Amino acids derivatized as orthophthalaldehyde derivatives, Supelco Supelcosil LC-18, 15×4.6 mm column, non-linear gradient from 100 % tetrahydrofuran (10 %):$KH_2PO_4$ (0.1M):KOAc (0.2M) to 100% methanol (80%):acetic acid (0.N, 20%) over 55 minutes) before and after removal of the 50% $^2H$, $^{13}C$, $^{15}N$-labeled glutamic acid. The HPLC chromatograms were substantially identical except that the peak corresponding to glutamic acid was completely removed following passage through the acetate resin.

Example 10

9-fluorenylmethyl chloroformate (3.88 g, 15 mmol) and N-hydroxysuccinimide (1.73 g, 15 mmol) were dissolved in dioxane (20 ml) and treated with triethylamine (2.09 ml, 15 mmol). The resulting suspension was stirred for 15 min.

50% $^2$H, $^{13}$C, $^{15}$N-labeled glutamic acid (1.88 g, 12 mmol) and anhydrous sodium carbonate (2.54 g, 20 mmol) were dissolved in water and the resulting solution added to the suspension of 9-fluorenylmethyl-N-hydroxysuccinylformate prepared above. The resulting suspension was stirred at room temperature overnight.

The solution was evaporated to dryness and partitioned between chloroform (approx 200 ml) and water (approx 200 ml). The aqueous layer was acidified to approximately pH 2 with concentrated hydrochloric acid and extracted with ethyl acetate. The organic layer was dried (anhydrous magnesium sulfate) and evaporated under reduced pressure to give the putative N-fluoroenylmethyl 50% $^2$H, $^{13}$C, $^{15}$N-labeled glutamic acid derivative as a powder.

Trioxane (2.70 g, 30 mmol) and p-toluenesulfonic acid (trace) were added to the powder obtained above, the whole suspended in toluene and refluxed overnight. The solution was then allowed to cool and evaporated to a gum under reduced pressure. The residue was partitioned between ethyl acetate (approx 200 ml) and water (approx 200 ml) and the aqueous layer dried (anhydrous magnesium sulfate) and evaporated to dryness under reduced pressure to give the oxazolidinone as a powder.

The powder thus obtained was dissolved in anhydrous tetrahydrofuran (50 ml), treated with diisopropylcarbodiimide (2.06 ml, 13.1 mmol) and stirred for 30 mins at room temperature before being cooled in a dry ice/acetone bath.

Separately, $^{15}$N-ammonium chloride (2.86 g, 52.5 mmol) was added to a Schlenk tube and dissolved in dimethylsulfoxide (25 ml). The tube tap was closed and the solution frozen by immersion in a dry ice/acetone bath. The tap was reopened and sodium hydride (2.1 g, 60% dispersion in oil, 52.5 mmol, prewashed with hexane and dried under nitrogen) added to the tube. The tap was immediately closed and the side arm connected to a bubbling tube placed in the cooled flask containing the oxazolidinone derivative.

The dimethylsulfoxide solution in the Schlenk tube was allowed to thaw, whereupon $^{15}$N-ammonia was evolved which condensed in the oxazolidinone solution. After all the $^{15}$N-ammonia had distilled over, a clamp was placed over the bubbler tube thereby closing it. The oxazolidinone solution was allowed to warm to room temperature overnight.

Water (approximately 2 ml) was added to the resulting solution and the whole stirred for 30 minutes. The resulting solution was then evaporated to dryness sunder reduced pressure.

The residue was dissolved in ethanol (50 ml) and water (10 ml). The solution was treated with sodium hydroxide (1M, 10.15 ml) and refluxed for 2.5 hours to give the N-protected glutamine derivative. On cooling, the solution was treated with piperidine (1.04 ml, 10.5 mmol) and the whole stirred at room temperature overnight.

The resulting solution was evaporated to dryness under reduced pressure and partitioned between chloroform (approximately 100 ml) and water (approximately 100 ml). The aqueous layer was extracted with diethylether (approximately 100 ml) and the pH adjusted to approximately 7 with glacial acetic acid. The resulting solution was passed through a column of Dowex 1X2-400 ion exchange resin (NH$^+$ form, 20 g) and evaporated to dryness. The residue was dissolved in water (approximately 100 ml) and passed through a column of Dowex 50X8-100 ion exchange resin (acetate form, 10 g) and the resulting solution evaporated to dryness under reduced pressure. The 50% $^2$H, $^{13}$C, $^{15}$N-labeled glutamine thus produced did not crystalize.

A portion of the material was therefore dissolved in a minimum of 5:1.5:1 v/v/v isopropyl alcohol:water:glacial acetic acid, added to a EM Separations LiChroprep Diol column (50×2.5 cms) and eluted with 5:1 v/v/v isopropyl alcohol:glacial acetic acid. The appropriate fractions were combined and evaporated under reduced pressure to give 50% $^2$H, $^{13}$C, $^{15}$N-glutamine as a gum.

I claim:

1. A method for determining three-dimensional structural information of a protein, which comprises the steps of (a) growing, under protein-producing conditions, a mammalian or insect cell culture which is capable of producing the protein of interest in a nutrient medium which contains all amino acids that are essential for growth of the cells and which contains assimilable sources of carbohydrate, essential minerals and growth factors, wherein the amino acids and any other substrate used by the cells for protein synthesis in such nutrient medium are substantially isotopically labeled; (b) isolating the labeled protein from the nutrient medium in substantially labeled form and (c) subjecting the protein to NMR spectroscopic analysis to determine information about its three-dimensional structure.

2. The method of claim 1, wherein the isotopically labeled amino acids in such nutrient medium contain carbon atoms substantially all of which are $^{13}$C.

3. The method of claim 1, wherein the isotopically labeled amino acids in such nutrient medium contain carbon atoms substantially all of which are $^{13}$C. and substantially all of the nitrogen atoms in the amino acids in such nutrient medium are $^{15}$N.

4. The method of claim 2 or 3, wherein a sufficient proportion of the hydrogen atoms in the amino acids in such nutrient medium are $^2$H so as to enchance the resolution of signals generated in the NMR spectroscopic analysis as compared to those generated in the NMR spectroscopic analysis of the non-deuterated form of the labeled protein.

5. The method of claim 2, wherein the isotopically labeled amino acids contain hydrogen atoms from about 20% to about 100% of which are $^2$H.

6. The method of claim 2, wherein said assimilable sources of carbohydrates contain carbon atoms substantially all of which are $^{13}$C and contains hydrogen atoms from about 20% to about 100% of which are $^2$H.

7. A method for determining three-dimensional structural information of a first molecule while such first molecule is complexed to a second molecule, wherein at least one of such molecules is a protein, which comprises the steps of (a) producing the first molecule in a form substantially labeled with a stable NMR-active isotope; (b) forming a complex between the first and second molecules and (c) subjecting the complex to NMR spectroscopic analysis to determine information about the three-dimensional structure of the first molecule.

8. The method of claim 7, which further comprises, prior to step (b), producing the second molecule in a form substantially labeled with deuterium.

9. The method of claim 7, wherein the first molecule is a protein and is produced by a method comprising the steps of (a) growing, under protein-producing conditions, a mammalian or insect cell culture that is capable of producing the protein of interest in a nutrient medium which contains all amino acids that are essential for growth of the cells and which contains assimilable sources of carbohydrate, essential minerals and growth factors, wherein the amino acids are substantially labeled with an NMR-active isotope; and (b)

isolating the labeled protein from the nutrient medium in substantially labeled form.

10. The method of claim 9, wherein the second molecule is a protein and is produced by a method comprising the steps of (a) growing, under protein-producing conditions, a mammalian or insect cell culture that is capable of producing the protein of interest in a nutrient medium which contains all amino acids that are essential for growth of the cells and which contains assimilable sources of carbohydrate, essential minerals and growth factors, wherein the amino acids are substantially labeled with $^2$H; and (b) isolating the labeled protein from the nutrient medium in substantially labeled form.

11. The method of claim 10, wherein the first molecule is a protein and is produced by a method comprising the steps of (a) growing, under protein-producing conditions, a mammalian or insect cell culture that is capable of producing the protein of interest in a nutrient medium which contains all amino acids that are essential for growth of the cells and which contains assimilable sources of carbohydrate, essential minerals and growth factors, wherein the amino acids are substantially labeled with an NMR-active isotope; and (b) isolating the labeled protein from the nutrient medium in substantially labeled form.

12. The method of claim 7, 8, 9, 10, or 11 wherein the NMR-active isotope is $^{13}$C.

13. The method of claim 7, 8, 9, 10, or 11, wherein the first molecule is doubly labeled with $^{13}$C and $^{15}$N.

14. The method of claim 11, wherein the NMR-active isotope is $^{13}$C or both $^{13}$C and $^{15}$N and a sufficient proportion of the hydrogen atoms in the amino acids in the nutrient medium used for preparing the first molecule are $^2$H so as to enhance the resolution of signals generated in the NMR spectroscopic analysis as compared to those generated in the analysis of the non-deuterated form of the labeled protein.

15. The method of claim 14, wherein from about 20% to about 100% of the hydrogen atoms in the amino acids in the nutrient medium used for preparing the first molecule are $^2$H.

16. A method for preparing isotopically labeled cysteine, which comprises (a) reacting isotopically labeled cysteine, either as the free amino acid present in an amino acid mixture or as a cysteine residue in a polypeptide, with a halobenzyl compound of the formula

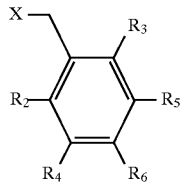

to form a protected thioether of the formula

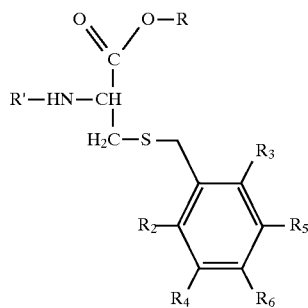

wherein X is a halogen; R and R' are each hydrogen, when the starting material is free cysteine or represent adjacent amino acid residues when the starting material is a polypeptide, at least one of $R_2$–$R_6$ is either an acidic group selected from carboxy, $C_1$–$C_4$ carboxyalkyl and $C_1$–$C_4$ carboxyalkoxy or a basic group selected from $C_2$–$C_4$ dialkylamino, $C_3$–$C_6$ dialkylaminoalkyl or $C_3$–$C_6$ dialkylaminoalkoxy and the remaining $R_2$–$R_6$ groups are either singly or in combination, hydrogen, halogen, $C_1$–$C_6$ alkyl or $C_1$–$C_6$ alkoxy;

(b) isolating the protected thioether; and (c) deprotecting the protected thioether to produce isotopically labeled cysteine.

17. The method of claim 16, wherein the isotopically labeled cysteine is present as a cysteine residue in a polypeptide and wherein step (b) comprises (i) hydrolyzing the polypeptide to form an amino acid mixture which contains the protected thioether and (ii) isolating the protected thioether from the amino acid mixture by ion exchange chromatography.

18. The method of claim 17, wherein the halobenzyl compound is 4-chloromethylbenzoic acid.

19. An isotopically labeled cysteine preparation, in which substantially all of the carbon atoms are $^{13}$C, substantially all of the nitrogen atoms are $^{15}$N and from about 20% to about 100% of the hydrogen atoms are $^2$H.

20. A method for preparing isotopically labeled glutamine or asparagine which comprises (a) reacting isotopically labeled glutamic or aspartic acid with an N-protecting group to form an N-protected amino acid of the formula

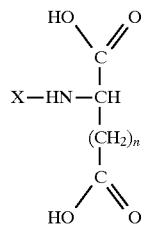

(b) cyclizing the N-protected amino acid to form an oxazolidinone of the formula

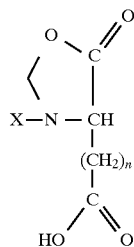

(c) reacting the oxazolidonone with ammonia under amide-forming conditions to form a cyclic amide derivative of the formula

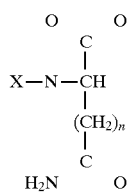

(d) hydrolyzing the cyclic amide derivative to form an N-protected amino acid of the formula

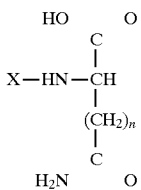

(e) deprotecting the N-protected amino acid to form isotopically labeled glutamine or asparagine, wherein n is 1 or 2 and X is an amine protective group.

21. A glutamine preparation in which substantially all of the carbon atoms are $^{13}C$, substantially all of the nitrogen atoms are $^{15}N$ and from about 20% to about 100% of the hydrogen atoms are $^{2}H$.

22. An asparagine preparation in which substantially all of the carbon atoms are $^{13}C$, substantially all of the nitrogen atoms are $^{15}N$.

23. The preparation of claim 22, wherein from about 20% to about 100% of the hydrogen atoms are $^{2}H$.

24. The method of claim 1, wherein subjecting the protein to NMR spectroscopic analysis comprises the steps of (a) forming a complex between the protein and a second molecule; and (b) subjecting the complex to NMR spectroscopic analysis to determine information about the three-dimensional structure of the protein.

25. A method for determining three dimensional structural information of a protein, which comprises the steps of (a) growing, under protein-producing conditions, a mammalian or insect cell culture which is capable of producing the protein of interest in a nutrient medium which contains all amino acids that are essential for growth of the cells and which contains assimilable sources of carbohydrate, essential minerals and growth factors, wherein the amino acids and any other substrate used by the cells for protein synthesis in such nutrient medium are substantially isotopically labeled; (b) isolating the labeled protein from the nutrient medium in substantially labeled form; (c) forming a complex between the protein and a second molecule; and (d) subjecting the complex to NMR spectroscopic analysis to determine information about the three-dimensional structure of the protein.

26. The method of claim 25, which further comprises, prior to step (b), producing the second molecule in a form substantially labeled with deuterium.

27. The method of claim 25, wherein the NMR-active isotope is $^{13}C$.

28. The method of claim 25, wherein the protein is doubly labeled with $^{13}C$ and $^{15}N$.

* * * * *

UNITED STATES PATENT AND TRADEMARK OFFICE
CERTIFICATE OF CORRECTION

PATENT NO. : 5,817,474
DATED : October 6, 1998
INVENTOR(S) : Jonathan Miles Brown It is certified that error appears in the above-identified patent and that said Letters Patent is hereby corrected as shown below:

Column 26, claim 3,
Line 30, delete the "." after C.

Signed and Sealed this

Twenty-seventh Day of November, 2001

Attest:

*Attesting Officer*

NICHOLAS P. GODICI
*Acting Director of the United States Patent and Trademark Office*